(12) United States Patent
Seeber et al.

(10) Patent No.: US 8,680,340 B2
(45) Date of Patent: Mar. 25, 2014

(54) PRECIOUS METAL CATALYSTS WITH LOW METAL LOADING FOR OXIDATIVE DEHYDROGENATIONS

(75) Inventors: Georg Seeber, Lambsheim (DE); Dirk Grossschmidt, Mannheim (DE); Torsten Mäurer, Lambsheim (DE); Christian Baltes, Neustadt (DE)

(73) Assignee: BASF SE, Ludwigshafen (DE)

( * ) Notice: Subject to any disclaimer, the term of this patent is extended or adjusted under 35 U.S.C. 154(b) by 27 days.

(21) Appl. No.: 13/457,644

(22) Filed: Apr. 27, 2012

(65) Prior Publication Data

US 2012/0277476 A1    Nov. 1, 2012

Related U.S. Application Data

(60) Provisional application No. 61/479,864, filed on Apr. 28, 2011.

(51) Int. Cl.
| | | |
|---|---|---|
| *C07C 45/27* | (2006.01) | |
| *B01J 37/34* | (2006.01) | |
| *B01J 21/16* | (2006.01) | |
| *B01J 23/00* | (2006.01) | |

(52) U.S. Cl.
USPC ............ 568/471; 568/473; 502/243; 502/347

(58) Field of Classification Search
USPC ........................... 568/471, 473; 502/243, 347
See application file for complete search history.

(56) References Cited

U.S. PATENT DOCUMENTS

| | | | |
|---|---|---|---|
| 4,165,342 | A | 8/1979 | Dudeck et al. |
| 5,149,884 | A | 9/1992 | Brenner et al. |
| 5,668,077 | A | 9/1997 | Klopries et al. |
| 5,989,648 | A | 11/1999 | Phillips |
| 6,013,843 | A | 1/2000 | Aquila et al. |
| 6,689,192 | B1 | 2/2004 | Phillips et al. |
| 2005/0233380 | A1 | 10/2005 | Pesiri et al. |
| 2011/0015446 | A1 | 1/2011 | Maurer et al. |

FOREIGN PATENT DOCUMENTS

| | | |
|---|---|---|
| DE | 20 20 865 A1 | 11/1971 |
| DE | 27 15 209 A1 | 10/1978 |
| DE | 102008014910 A1 | 9/2009 |
| EP | 244632 A2 | 11/1987 |
| EP | 357292 | 3/1990 |
| EP | 619 142 A1 | 10/1994 |
| EP | 0881206 A1 | 12/1998 |
| GB | 1338698 A | 11/1973 |
| WO | WO-2006/042109 A2 | 4/2006 |

*Primary Examiner* — Sikarl Witherspoon
(74) *Attorney, Agent, or Firm* — Novak Druce Connolly Bove + Quigg LLP

(57) ABSTRACT

A method of production of a catalyst that has 0.05-0.25 wt. % of precious metal, preferably for the oxidative dehydrogenation of olefinically unsaturated alcohols, comprising the following steps
a) producing a D.C. plasma,
b) introducing the metal and support material into the plasma,
c) evaporating the metal and support material or "shattering" the solid bodies of metal and support material in the plasma, and reaction of the particles,
d) cooling, so that very small particles of composite material are obtained,
e) applying the composite material on the catalyst support proper, the correspondingly produced catalyst and use thereof.

14 Claims, 2 Drawing Sheets

Fig. 3
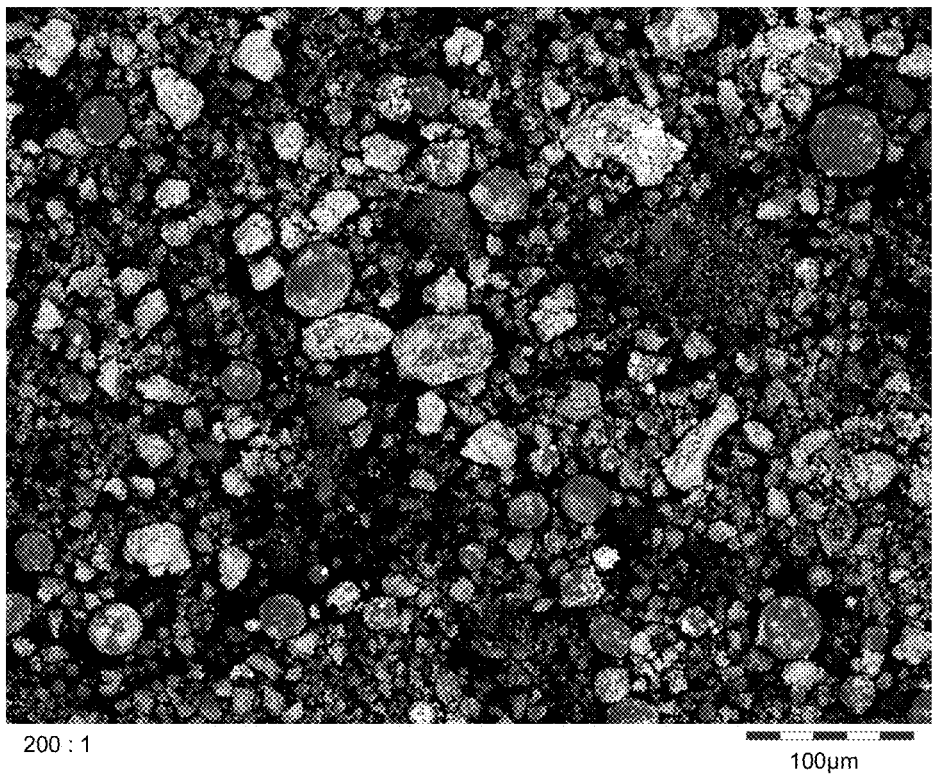
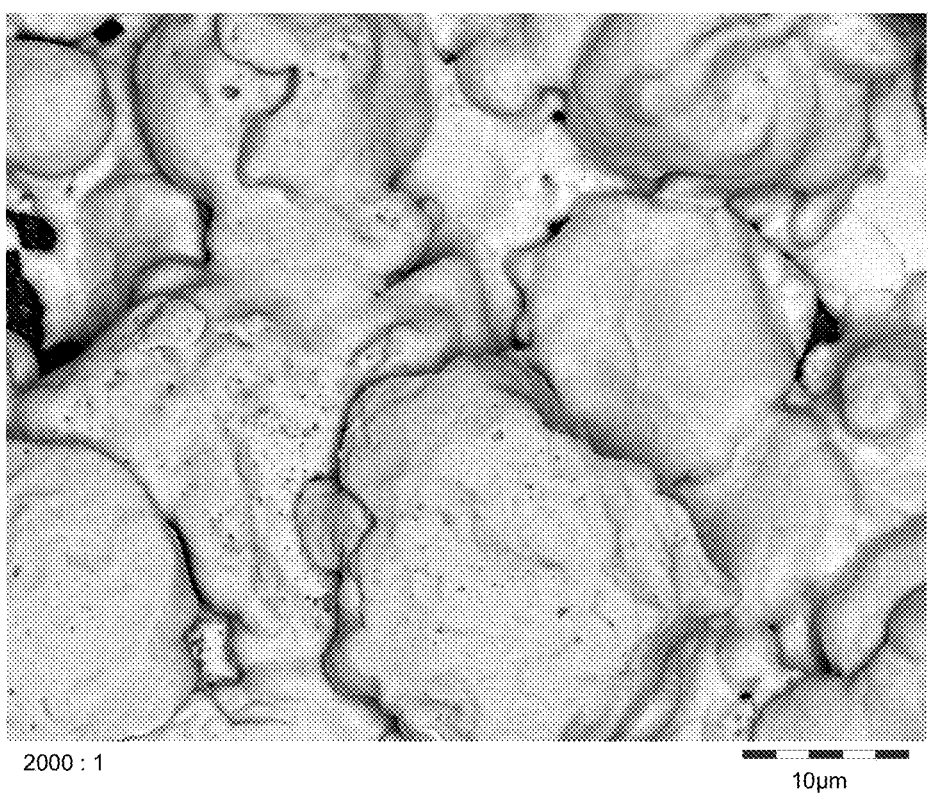
Fig. 4

PRECIOUS METAL CATALYSTS WITH LOW METAL LOADING FOR OXIDATIVE DEHYDROGENATIONS

CROSS-REFERENCE TO RELATED APPLICATIONS

This application claims benefit (under 35 USC 119(e)) of U.S. Provisional Application 61/479,864, filed Apr. 28, 2011, which is incorporated by reference.

All documents cited in the present application are incorporated by reference in their entirety in the present disclosure.

The present invention relates to the use of a supported precious metal-containing catalyst for the production of olefinically unsaturated carbonyl compounds from olefinically unsaturated alcohols by oxidative dehydrogenation and corresponding supported precious metal-containing catalysts and production thereof.

PRIOR ART

The production of alpha,beta-unsaturated carbonyl compounds by oxidative dehydrogenation on suitable catalysts is known by a person skilled in the art and is widely described in the literature.

Thus, DE-B-20 20 865 describes a method of production of alpha,beta-unsaturated carbonyl compounds, wherein, according to the description, alloys and metal compounds, especially some metal oxides of the subgroup elements, can be used as dehydrogenation catalysts. Furthermore, it is stated in this document that the catalysts can be used in pure form and in the form of mixed catalysts with or without supporting substance. Zinc oxide, cadmium oxide and manganese oxide and mixed catalysts from the metals Cu, Ag and/or Zn are mentioned as being especially suitable. This document does not give any further information about the production of the catalyst.

EP-A 0 881 206 describes a method for continuous commercial production of unsaturated aliphatic aldehydes in a tube-bundle reactor. The preferred catalysts for this method are stated to be supported silver catalysts, which consist of spheres of an inert support material, which are coated with 0.1 to 20 wt. %, relative to the amount of support, of a layer of metallic silver in the form of a smooth, abrasion-resistant shell. Furthermore, a specified ratio of the largest diameter of the coated catalyst spheres to the inside diameter of the reaction tube should preferably be maintained.

From DE-A 27 15 209, a method is known for the production of 3-alkylbuten-1-als, using a catalyst with a total layer thickness of 5 to 35 mm and 2 or more layers of silver and/or copper crystals. The production of the catalyst with several layers of precious metal is in this case relatively expensive.

A method of production of ethylene oxide is known from EP A 0 357 292. The catalysts used in this method are silver catalysts, wherein the silver is applied on a porous heat-resistant support with a particular BET specific surface. According to the information in this document, the silver can be applied to the support as a suspension of silver or silver oxide in a liquid medium, for example water, or by impregnation of the support with a solution of a silver compound. This silver compound is then reduced to elemental silver by thermal treatment. This document does not contain any information on possible use of the resultant silver-containing supported catalysts for the production of ethylenically unsaturated carbonyl compounds.

Silver catalysts for the oxidation of ethylene to ethylene oxide, which are obtained by impregnation with an aqueous (colloidal) solution of a silver salt, are known from EP-A 0 619 142.

Furthermore, precious metal-containing catalysts, which are obtained by applying a complexed, sparingly soluble compound of a precious metal from suspension or solution on a support and subsequent thermal treatment, are known from the previously unpublished German patent application DE 10 2008 014 910.1.

Moreover, supported silver catalysts (approx. 6 wt. %) for use in the oxidative dehydrogenation of isoprenol to prenal, production of which is based on a flame-spraying process, are known from the prior art (cf. example 1 in DE 10 2008 014 910.1).

In the flame-spraying process, a metal is "melted" in an acetylene flame and the liquefied metal is "sprayed" on the catalyst support (with subsequent solidification of the metal on the support surface).

Problem:

3-Methylbut-2-en-1-al, also known by the trivial name prenal, is an important precursor for citral, which in its turn is an important product for a large number of chemical syntheses. The catalysts described in the literature for the production of prenal (3-methylbut-2-en-1-al) still contain relatively large amounts of precious metal, essentially silver, so that they are still relatively expensive. The problem to be solved by the present invention is, accordingly, to provide precious metal-containing support catalysts for oxidative dehydrogenations, in particular for the synthesis of prenal from isoprenol (3-methylbut-3-en-1-ol), which, with comparable performance data (activity and selectivity), contain smaller amounts of precious metal and therefore are less expensive.

Another problem to be solved by the present invention is to provide a method of production of these less expensive catalysts.

A further problem to be solved by the present invention is the use of the catalysts according to the invention or produced according to the invention for oxidative dehydrogenations, in particular for the synthesis of prenal from isoprenol (3-methylbut-3-en-1-ol).

Solution:

The problem is solved by a method of production of a catalyst, which preferably has 0.05-0.25 wt. % of precious metal, preferably for the oxidative dehydrogenation of olefinically unsaturated alcohols, comprising the following steps
a) producing a D.C. plasma, so that an extremely high temperature is produced,
b) introducing the metal and support material into the plasma,
c) evaporating the metal and support material or "shattering" the solid bodies, and reaction of the particles,
d) cooling, so that very small particles of a composite material are obtained,
e) applying the composite material on the catalyst support proper.

Furthermore, the problem is solved by the use of a catalyst produced in this way, which preferably has 0.05-0.25 wt. % of precious metal, for the production of olefinically unsaturated carbonyl compounds from olefinically unsaturated alcohols by oxidative dehydrogenation.

Finally, a catalyst that preferably has 0.05-0.25 wt. % of precious metal, preferably for the oxidative dehydrogenation of olefinically unsaturated alcohols, produced by the method described, contributes to solution of the problem according to the invention.

Definitions Of Terms:

Within the scope of the present invention, all amounts, unless stated otherwise, are to be understood as amounts by weight.

Within the scope of the present invention, the term "room temperature" means a temperature of 20° C. Unless stated otherwise, temperatures are given in degrees Celsius (° C.).

Unless stated otherwise, the reactions or process steps described are carried out at normal pressure/atmospheric pressure, i.e. at 1013 mbar.

Spherical means, within the scope of the present invention, that the primary particles in question are spheroidal and, in transmission electron microscopy (TEM), comparably with ideal spheres, do not display any preferred direction or preferred edges.

Within the scope of the present invention, all particle sizes were/are determined by means of SEM (scanning electron microscopy).

DETAILED DESCRIPTION

The present invention relates to a method of production of a catalyst, preferably for the oxidative dehydrogenation of olefinically unsaturated alcohols, comprising the following steps
a) producing a D.C. plasma ("ionized gas"), so that an extremely high temperature is produced (far higher than in an acetylene flame),
b) introducing the metal and support material into the plasma,
c) evaporating the metal and support material or "shattering" the solid bodies and reaction of the particles,
d) cooling, so that very small particles of a composite material are obtained,
e) applying the composite material on the catalyst support proper, preferably made of steatite, especially preferably steatite spheres of approx. 2 mm diameter.

Furthermore, the present invention relates to the use of a catalyst produced in this way for the production of olefinically unsaturated carbonyl compounds from olefinically unsaturated alcohols by oxidative dehydrogenation.

Finally the present invention relates to a catalyst, preferably for the oxidative dehydrogenation of olefinically unsaturated alcohols, produced by the method described.

In preferred embodiments of the present invention, both in the method according to the invention, and in the use according to the invention and the catalyst per se according to the invention, the catalyst has in each case 0.05-0.25 wt. % of precious metal.

In process steps a) to d) of the present invention, composites of precious metal and support material are produced, wherein the precious metal particles, preferably silver particles, are present in the composite at an average particle size of <10 nm.

The proportion of precious metal is about 30 wt. %, relative to the composite material.

In step d) of the method according to the invention, accordingly a composite material of 30 wt. % silver and remainder support material is obtained. This can be seen from the SEM micrograph in FIG. 3.

In one embodiment of the present invention, the composite material has for example a particle size range of 0.5-100 μm, preferably 2-80 μm. In one embodiment of the present invention the composite material then has for example average diameters of 5-30 μm, preferably 10-20 μm.

This composite material is then applied in step e) on the support proper, preferably with a size of 1.8 to 2.2 mm, preferably using steatite, in particular in the form of spheres, as the support.

The support materials can be the same or different in steps b) and e). It is preferred if the support materials in steps b) and e) are the same.

There are therefore clear distinctions from the prior art both in the production of the catalysts and in the catalysts themselves. The most important features are:
  the nanoscale dimension of the silver particles, preferably 1-50 nm, especially preferably 1-20 nm, particularly preferably 1-10 nm within the steatite matrix,
  the high activity of these catalysts despite the very low silver contents,
  presence of a composite of silver and support material, which is applied on the support proper.

In contrast, silver is present macroscopically in the catalyst according to the prior art (cf. FIG. 4).

The present invention further describes the use of precious metal catalysts obtained by the method of production according to the invention, with low metal loading, in particular to be used for oxidative dehydrogenations.

The low metal loading on the catalysts according to the invention, produced by the method according to the invention, in comparison with the far higher metal loadings in conventional catalysts, is, surprisingly, sufficient for carrying out oxidative dehydrogenations.

This is achieved, within the scope of the present invention, because of the high dispersion of the precious metal loading on the catalyst; in particular, the high dispersion of the precious metal loading on the catalyst is achieved because the catalyst is produced by means of the method described.

Owing to the marked decrease in precious metal loading of the catalysts according to the invention, there are considerable savings in raw material costs in comparison with conventional catalysts, which represents an enormous economic advantage (the precious metal being the price determinant).

Within the scope of the present invention, supported precious metal catalysts with a small proportion of precious metal were found, which can preferably be used for the oxidative dehydrogenation of 3-methylbut-3-en-1-ol (MBE, isoprenol) to 3-methylbut-2-en-1-al (MBA, prenal).

The catalysts of the present invention have 0.05-0.25 wt. % of precious metal supported on an inert support, most preferably steatite, and surprisingly achieve comparable performance data, in particular with respect to activity and selectivity, compared with standard catalysts (6 wt. % Ag supported on steatite) at considerably lower costs.

Preferably, the precious metals used are Cu, Au, Ag, Pd, Pt, Rh, Ru, Ir or Os, and optionally W, or mixtures thereof. Especially preferably, Cu and Ag or mixtures thereof are used as precious metals. The use of Ag is quite especially preferred.

When using mixtures, there is no particular restriction on the mixture ratio.

Within the scope of the present invention, in one variant, further additives suitable as promoters can be added to the catalysts. Only alkali, alkaline earth and transition metals (such as Li, Rb, Cs, Ca, Mg, V, Co, Ni, Ir or Re) will be mentioned here as examples.

Suitable support materials that can be used for the catalysts within the scope of the present invention are known per se by a person skilled in the art and are described in the literature, to which reference is made here for further details.

In a preferred embodiment of the present invention, the support materials have minimum possible porosity and have a maximum BET surface of $0.1\ m^2/g$.

In a preferred embodiment of the present invention the support materials are spherical and have an average diameter of 1.3 to 2.5 mm, preferably 1.8 to 2.2 mm.

Preferred support materials are steatite, aluminum oxides or aluminosilicates.

In some cases hydrotalcites have also proved suitable.

Hydrotalcite generally means a layered material with the chemical formula $[M(II)_{1-x}M(III)_x(OH)_2]^{x+}[A_{n/x}]^{n-}*m\ H_2O$, where M(II) stands for a divalent metal, M(III) for a trivalent metal, A is an anion intercalated in the lattice, m stands for the number of intercalated water molecules and x stands for the molar ratio M(II)/[M(II)+M(III)]. Usually x is in the range from 0.2 to 0.33, which corresponds to molar ratios of M(II) to M(III) in the range from 2 to 4. As divalent metals, we may mention for example Mg, Fe, Ni, Co, Zn and Mn, as trivalent metals Al, Ga, In, Co and Mn. The possibility of simultaneous presence of several divalent or trivalent metals in different molar proportions increases the structural diversity of the suitable hydrotalcites.

As minerals of the hydrotalcite group, we may mention, purely as examples, manasseite, pyroaurite, sjogrenite, stichtite, barbertonite, desautelsite, meixnerite or takovite, which are described in the literature and whose composition is known by a person skilled in the art. A preferred hydrotalcite has the composition $Mg_6Al_2(CO_3)(OH)_{16}*4\ H_2O$.

An especially preferred support material is steatite, a ceramic material based on natural raw materials, which consists of the main component soapstone $(Mg(Si_4O_{10})(OH)_2)$, a natural magnesium silicate. Furthermore, it can also contain additives of clay and feldspar or barium carbonate.

Especially preferably steatite is used according to the invention both in step b) and in step e).

Suitable steatites are known by a person skilled in the art and are commercially available, e.g. from CeramTec or Saint-Gobain N or Pro.

The precious metal contents of the catalysts according to the invention, measured in wt. %, relative to the support material, are, within the scope of the present invention, in the range from 0.05 to 0.25 wt. %, preferably in the range from 0.08 to 0.2 wt. % and especially preferably in the range from 0.09 to 0.12 wt. %, in each case relative to the total weight of the catalyst particles.

The advantages achieved within the scope of the present invention are essentially that equal performance data (activity and selectivity) are achieved with a smaller amount of precious metal, resulting in a saving on the raw material costs of the precious metal catalyst.

The fundamental method of production of composite materials in the arc plasma is described for example in U.S. Pat. No. 6,689,192 B1 and U.S. Pat. No. 5,989,648.

A corresponding method comprising synthesis and powder separation is described for example in WO 2006/042109.

In a preferred embodiment of the present invention, the composite materials according to the invention, i.e. the catalysts according to the invention comprising support material and precious metal, are produced observing the following parameters.

Production of the plasma and synthesis of the composite material precious metal on support, in particular silver on steatite, can take place in the plant usually employed for this.

For example, a microwave plasma or an arc plasma can be used for producing the D.C. plasma.

In a preferred embodiment, a so-called plasma-spray gun is used for producing the plasma. This consists of a housing serving as the anode and a water-cooled copper cathode arranged centrally therein, wherein an electric arc of high energy density burns between the cathode and the housing. The plasma gas supplied ionizes to form the plasma and leaves the gun at high velocity (e.g. about 300 to 700 m/s) at temperatures for example in the range from 15000 to 20000 kelvin.

The starting materials—precious metal and support, in particular silver and steatite—are introduced directly into this plasma jet for treatment, are evaporated there and then, by cooling again, are converted back to the solid phase. Suitable particle sizes are between 1 and 100 μm, and a narrow particle size distribution between 1 and 10 μm is especially preferred.

A gas or gas mixture is used for generating the plasma. A distinction is made between the plasma gas proper, the carrier gas used for supplying the starting materials and the enveloping gas used (gas stream that envelopes the treatment zone proper, e.g. to prevent deposits on the walls). Plasma gas, enveloping gas and carrier gas can all three have the same composition, two of the gases can have the same composition, or all three can have a different composition.

Typical powers introduced into the plasma are in the range from a few kW up to several 100 kW. Sources for plasma of higher power can basically also be used for the treatment.

The types of gases that can be used are the usual gases known by a person skilled in the art, and preferably inert gases are used, especially preferably argon.

During the treatment in the plasma gas, after successful nucleation, first there is formation of nanoparticulate primary particles, which undergo further particle growth by processes of coagulation and coalescence. Particle formation and growth take place in the whole treatment zone and can even continue after leaving the treatment zone until rapid cooling is applied.

During treatment of a mixture of precious metal and support, in particular silver and steatite, nanoparticulate product mixtures are formed. The particle formation processes can be controlled, as well as by the composition and concentration of the feed materials, also by the nature and time point of cooling of the product being treated.

Within the scope of the present invention, the proportionate amounts can be varied widely, preferably from 5 to 35 wt. % of precious metal and 95 to 65 wt. % of support material introduced into the plasma.

Within the scope of the present invention, in a preferred embodiment 28 to 32 wt. % of precious metal and 72 to 68 wt. % of support material, especially preferably 30 wt. % of precious metal and 70 wt. % of support material are introduced into the plasma.

Preferably the treatment takes place under plasma conditions within the scope of the present invention at a temperature in the range from 600 to 25000° C.

As a rule, within the scope of the present invention, the residence time of the product mixture in the reaction zone is 0.002 seconds to 2 seconds, preferably 0.005 seconds to 0.2 seconds.

The treatment of the product materials in the plasma gas is followed, within the scope of the present invention, by a, preferably rapid, cooling of the treated product obtained, by the usual methods. Quenching with an inert gas stream (e.g. $N_2$) is used in one embodiment of the present invention. Quench rates of at least $10^4$ K/min are then preferred. The final temperature of the particle-laden gas should be approx. 80° C., at most 100° C. This cooling can be direct or indirect (or a combination of the two).

The required composites can be isolated by filtration from the cooled product stream (gas/solids).

Methods known by a person skilled in the art are suitable for coating a support material with the composite powder synthesized from the plasma. For example, powder coating may be mentioned. In this, the support material is moistened with liquid on a rotating turntable and the powder to be applied is distributed ideally simultaneously with moistening, slowly on the moving support particles. Suitable wetting liquid is for example pure water or water with auxiliaries, e.g. viscosity adjusting agents. These agents possess emulsifying and wetting action and are also called "surfactants". As examples of these agents, we may mention ethoxylates of alcohols, amines or amides and acids (e.g. Lutensol). Cellulose or cellulose derivatives (e.g. hydroxyethylcellulose) or glycerol are also suitable. The proportion of the auxiliary in water, if required at all, is suitably between 1 and 25 wt. %, preferably 2-20 wt. % and especially preferably between 3 and 10 wt. %. The turntable is operated with a rotary speed of 20-60 rev/min (revolutions per minute), preferably 30-50 rev/min, especially preferably 30-45 rev/min.

The wetting liquid is sprayed on the support, distributed as finely as possible. For example, two-component nozzles are suitable for this, and are operated with a gas, e.g. air or nitrogen, as propellant. The solid to be applied can be carefully sprinkled, but apparatus such as an oscillating chute is more suitable. The feed rate must be regulated so that the rotating support material does not stick together. The feed of liquid and solid is based on the mass of the coating material that is to be applied.

The catalysts according to the invention can be analyzed for example by means of TEM micrographs. It can be seen from these micrographs, which for example only show the composite material (i.e. before being applied on the support spheres), that in the case of the catalysts according to the invention, very small particles of precious metal (Ag in FIG. 1) are embedded in a steatite matrix.

Accordingly, in the catalysts according to the invention, the precious metal particles are not present as a layer in the form of a smooth, abrasion-resistant shell on the support, but as distributed particles embedded in the support surface.

The precious metal particles of the catalysts according to the invention are present on the support particles in the form of particles with an average size of <10 nm.

One advantage of the present invention is that owing to a high degree of dispersion of the precious metal loading on the catalyst or as a result of embedding of the precious metal particles in the support matrix, an especially large surface area and consequently increased activity of the catalyst is achieved.

In one embodiment of the present invention, in contrast to the prior art, which used massive support materials, the catalyst support is porous, so that there is better embedding of the precious metal particles in the support matrix.

In the present invention, an advantageous effect is that the precious metal particles, through being embedded in the support matrix, are far more resistant to sintering, than is the case with catalysts according to the prior art.

Especially advantageously, according to the invention, the supported precious metal-containing catalysts obtainable by the above procedure can be used for the production of 3-methylbut-2-en-1-al from 3-methylbut-3-en-1-ol. The product is also known by the trivial name prenal, the educt by the trivial name isoprenol.

In this especially preferred application, the reaction is preferably carried out in a tube-bundle reactor, as described for example in EP-A 881 206. For further details of the reactor geometry, reference should be made to said EP-A 881 206 and to EP-A 244 632.

By the use according to the invention of the or by the precious metal-containing supported catalysts according to the invention, it is possible to obtain prenal from isoprenol under mild temperature conditions with good yield and good selectivity. During reaction of isoprenol with the catalysts according to the invention, there is formation of a reaction mixture of 3-methylbut-3-en-1-al and 3-methylbut-2-en-1-al. The first-mentioned isomer then isomerizes, with base catalysis, in a subsequent step to the desired 3-methylbut-2-en-1-al.

For processing the reaction mixture, in a first stage the desired reaction product is separated by distillation from the unreacted educt. For this distillation to be conducted economically, advantageously an azeotrope is used, which consists of 70% 3-methylbut-3-en-1-al and 30% 3-methylbut-2-en-1-al. The latter is, as mentioned above, the thermodynamically favored product.

After the use according to the invention of the supported precious metal-containing catalyst obtainable as described above, prenal can be produced from isoprenol at good yield at lower temperatures and with good selectivity.

The various embodiments of the present invention, for example but not exclusively those of the various dependent claims, can be combined with one another in any way.

The invention will now be explained, referring to the following nonlimiting drawings and examples.

DESCRIPTION OF THE DRAWINGS

FIG. 3 shows a composite material according to step d) of the method according to the invention before (!) application on the steatite support. Silver appears as light spots; dark regions are to be ascribed to the steatite matrix.

FIG. 4 shows an example of an SEM micrograph of a catalyst according to the prior art produced in the flame-spraying process (6% Ag on steatite 2 mm spheres). As can be seen, the morphology of the silver is entirely different from the particles according to the present invention.

EXAMPLES

Example 1

Figure 1:
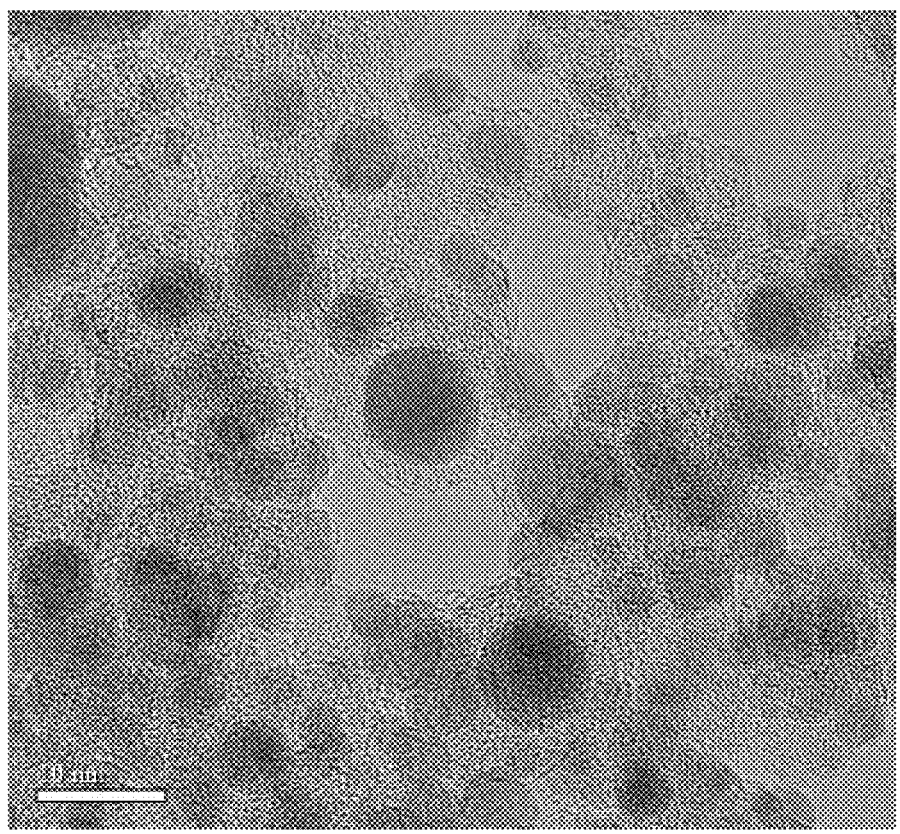
FIG. 1 shows a TEM micrograph of the catalyst particles produced according to step d) according to the invention of the method according to the invention according to example B) before (!) application on the steatite support. Dark spots show the silver particles (diameter up to 10 nm, average diameter approx. 6 nm), which are embedded in a matrix of steatite (gray shaded regions).
Figure 2:
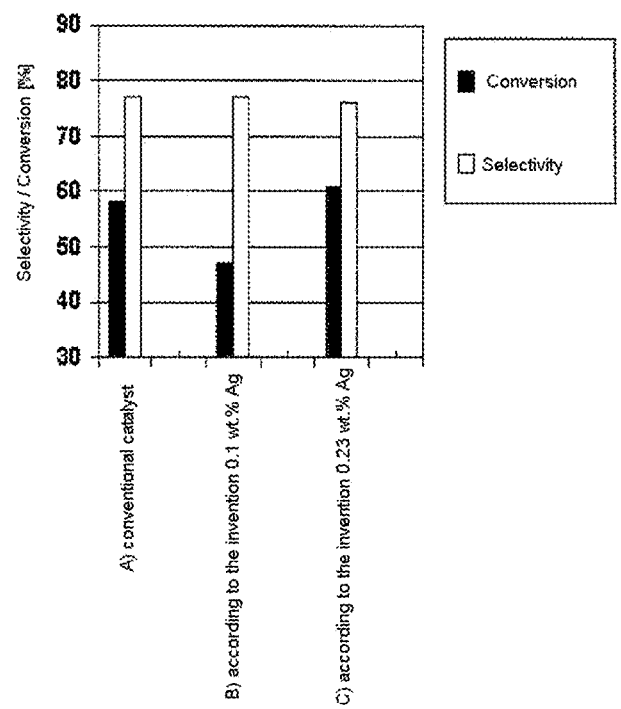
FIG. 2 is a diagram showing the respective selectivity and conversion of two catalysts according to the invention of examples B) and C) and a catalyst of the prior art according to comparative example A).

Production of Catalysts B and C According to the Invention

Synthesis of the Ag/steatite composite material by the plasma process.

The starting materials silver and steatite are prepared in a grain size fraction of 1-10 µm in the mixture ratio 30 wt. % silver to 70 wt. % steatite. The mixed powder is introduced via a nozzle into a $N_2$ carrier gas stream at a feed rate of 10 g/min and is supplied to a D.C. plasma (arc plasma, plasma and enveloping gas argon, apparatus made by Sulzer). The power is set at 80 kW. The residence time of the solid material in the plasma is set at approx. 10 milliseconds by adjusting the carrier gas stream. The product gas leaving the plasma is quenched to approx. 80° C. by a nitrogen stream maintained at room temperature. The composite particles formed in the quenching operation are separated from the gas stream in a suitable filter.

Coating of Steatite Spheres with Composite Particles

A turntable is filled with 1000 g of steatite spheres with a size of 1.8-2.2 mm (from CeramTec), and is operated with an Erweka AR 401 motor at a rotary speed of 40 rev/min.

Using a two-component nozzle from the company Spraying System Co., a mixture of 5 wt. % glycerol and 95 wt. % water is sprayed on the rotating spheres. Air is used as the propellant for the wetting liquid. Simultaneously with the liquid feed, 3.4 g (example B) or 7.8 g (example C) of the composite powder obtained by the plasma process is fed via an oscillating chute from the company Retsch onto the rotating steatite spheres. The liquid feed (approx. 5-10 g) is adjusted so that the spheres do not stick together.

Calcination of the Catalysts

The catalysts thus obtained are treated for 1 h in a preheated calcining kiln at 360° C. in air, then they are taken out and are cooled in a desiccator.

For examples A), B) and C), a quartz glass reactor was filled with 10 ml of the respective catalyst in each case. Then the reaction (production of 3-methylbut-2-en-1-al from 3-methylbut-3-en-1-ol) was carried out, evaporating 110 g/h MBE and 50 l/h air in a thin-film evaporator.

The results are shown in Table 1.

Example A

Comparative Example

A standard catalyst, which was produced by a flame-spraying process, was used for this example (cf. example 1 in DE 10 2008 014 910.1). This catalyst had a loading of 6 wt. % silver on a steatite support.

Example B

According to the Invention

A catalyst produced according to the invention with a loading of 0.1 wt. % silver on a steatite support was used for this example.

Example C

According to the Invention

A catalyst produced according to the invention with a loading of 0.23 wt. % silver on a steatite support was used for this example.

The same steatite spheres with a size of 1.8 to 2.2 mm were used as the steatite support in all the examples.

TABLE 1

|  | Conversion MBE | Selectivity MBA + IMBA |
| --- | --- | --- |
| a) conventional catalyst | 58.0 | 77.0 |
| b) 0.1 wt. % silver | 47.0 | 77.0 |
| c) 0.23 wt. % silver | 60.6 | 76.0 |

Catalysts B) and C), with lower loading of precious metal than standard catalyst A), showed an equally high selectivity as standard catalyst A).

The conversion was somewhat lower with catalyst B) with 0.1 wt. % Ag loading than with standard catalyst A); with catalyst C) with 0.23 wt. % Ag loading, comparable performance data (activity and selectivity) were achieved as with the standard catalyst A.

Therefore, in comparison with the conventional catalyst A), catalyst C) showed a comparable performance at greatly reduced silver loading and greatly reduced raw material costs.

Admittedly catalyst B) showed a somewhat lower conversion, but this is offset by the again greatly reduced raw material costs in comparison with catalyst C) (not even half the amount of Ag was needed).

The invention claimed is:

1. A method of production of a catalyst comprising the following steps
   a) producing a D.C. plasma,
   b) introducing a metal and a support material into the plasma
   c) evaporating the metal and the support material or "shattering" the solid bodies of metal and support material in the plasma, and reaction of the particles,
   d) cooling, so that very small particles of composite material are obtained,
   e) applying the composite material on the catalyst support proper.

2. The method as claimed in claim 1, wherein said metal is Cu, Au, Ag, Pd, Pt, Rh, Ru, Ir or Os or mixtures thereof.

3. The method as claimed in claim 1, wherein said support material is basic, acid or neutral support material.

4. The method as claimed in claim 3, wherein said support material is steatite, aluminum oxide, aluminosilicates or mixtures thereof.

5. The method as claimed in claim 1, wherein the support material is the same in steps b) and e).

6. The method as claimed in claim 1, wherein the catalyst has 0.05-0.25 wt. % of said metal.

7. A process for the production of olefinically unsaturated carbonyl compounds which comprises oxidative dehydrogenating olefinically unsaturated alcohols in the presence of a catalyst, wherein the catalyst was produced by a method as claimed in claim 1.

8. The process as claimed in claim 7, wherein the catalyst has 0.05-0.25 wt. % of precious metal.

9. The process as claimed in claim 8, wherein the precious metal is Cu, Au, Ag, Pd, Pt, Rh, Ru, Ir or Os or mixtures thereof.

10. The process as claimed in claim 7, wherein 3-methylbut-2-en-1-al is produced from 3-methylbut-3-en-1-ol.

11. A supported precious metal-containing catalyst produced by the method as claimed in claim 1.

12. The supported precious metal-containing catalyst as claimed in claim 11, wherein the catalyst has a precious metal loading of 0.05-0.25 wt. % of precious metal.

13. The supported precious metal-containing catalyst as claimed in claim 11, wherein the precious metal is in the form of particles with an average particle size of <10 nm on the catalyst support.

14. The supported precious metal-containing catalyst as claimed in claim 11, wherein the precious metal is silver and is in the form of particles with an average particle size of <10 nm on the catalyst support.

* * * * *